United States Patent [19]
Hoff

[11] Patent Number: 5,522,872
[45] Date of Patent: Jun. 4, 1996

[54] ELECTRODE-CONDUCTOR SLEEVE JOINT FOR CARDIAC LEAD

[75] Inventor: Eric Hoff, Cupertino, Calif.

[73] Assignee: Ventritex, Inc., Sunnyvale, Calif.

[21] Appl. No.: 351,866

[22] Filed: Dec. 7, 1994

[51] Int. Cl.⁶ ......................................... A61N 1/05
[52] U.S. Cl. .................. 607/119; 607/129; 607/120; 607/128; 607/127; 128/642
[58] Field of Search ........................... 128/642; 607/108, 607/119, 120, 126, 129, 127, 128

[56] References Cited

U.S. PATENT DOCUMENTS

| | | | |
|---|---|---|---|
| 4,161,952 | 7/1979 | Kinney et al. | 128/786 |
| 4,214,804 | 7/1980 | Little | 339/183 |
| 4,314,095 | 2/1982 | Moore et al. | 174/84 |
| 4,328,812 | 5/1982 | Ufford et al. | 128/786 |
| 4,355,646 | 10/1982 | Kallok et al. | 128/786 |
| 4,458,695 | 7/1984 | Peers-Trevarton | 128/786 |
| 4,662,382 | 5/1987 | Sluetz et al. | 128/785 |
| 4,679,572 | 7/1987 | Baker, Jr. | 128/786 |
| 4,784,161 | 11/1988 | Skalsky et al. | 128/785 |
| 4,827,932 | 5/1989 | Ideker et al. | 128/419 |
| 4,844,099 | 7/1989 | Skalsky et al. | 128/785 |
| 4,917,106 | 4/1990 | Olivier | 128/785 |
| 4,940,065 | 7/1990 | Tanagho et al. | 128/784 |
| 4,945,342 | 7/1990 | Steinemann | 174/113 |
| 4,989,617 | 2/1991 | Memberg et al. | 128/785 |
| 5,003,992 | 4/1991 | Holleman et al. | 607/120 |
| 5,007,435 | 4/1991 | Doan et al. | 607/119 |
| 5,203,348 | 4/1993 | Dahl et al. | 128/784 |
| 5,330,523 | 7/1994 | Campbell et al. | 607/129 |

Primary Examiner—Lee S. Cohen
Assistant Examiner—Stephen Huang
Attorney, Agent, or Firm—Steven M. Mitchell; Mark J. Meltzer

[57] ABSTRACT

A joint for cardiac stimulation lead has a sleeve that joins a conductor to an electrode. The conductor and electrode are inserted into passages formed through the sleeve and are bonded at least to the sleeve surface by laser welding, crimping, or resistance welding. The distal end of the conductor is attached to the sleeve and either the proximal end or the distal end of the electrode may be attached to the sleeve. The number, size, shape and positioning of passages in the sleeve are varied according to the desired lead configuration to allow passage of additional conductors through the joint.

21 Claims, 5 Drawing Sheets

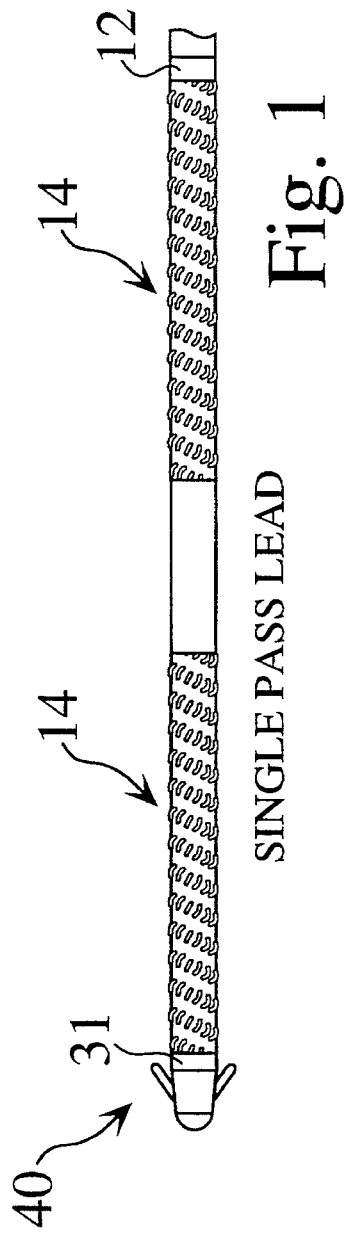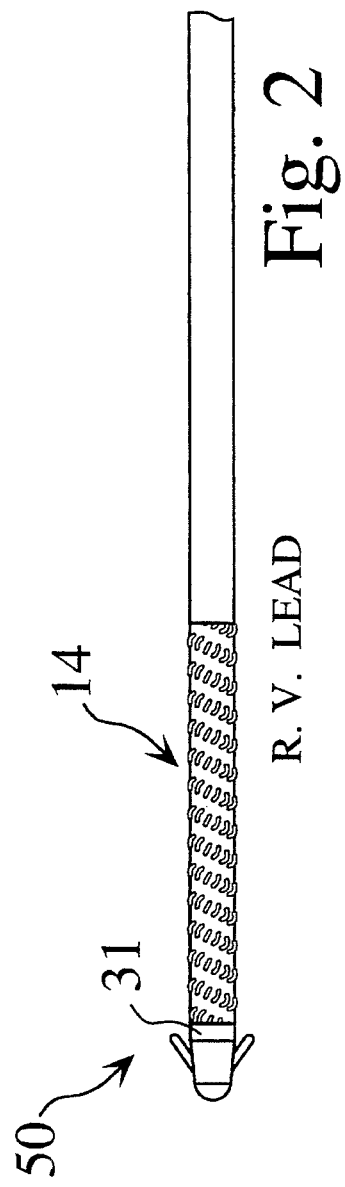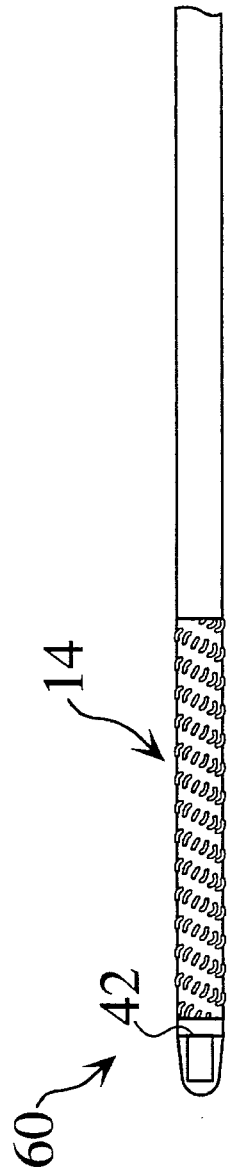

SECTION A-A

ELECTRODE-CONDUCTOR SLEEVE JOINT FOR CARDIAC LEAD

BACKGROUND OF THE INVENTION

TECHNICAL FIELD

The present invention relates to electrodes that are useful for medical applications. More particularly, the present invention relates to forming an electrically and mechanically reliable connection to a cardiac electrical stimulation and/or sensing electrode.

DESCRIPTION OF THE PRIOR ART

The use of pacing and defibrillation devices to stimulate or restore heart rhythm is well known in the prior art. These devices typically consist of a pulse generator that is implanted inside a patient's body and coupled to the patient's heart with an electrical lead. The lead includes an insulative lead body and a conductor portion for carrying the electrical pulses from the pulse generator and an electrode portion that makes actual electrical contact with the patient's heart.

It is imperative that surgical procedures for implanting electrical leads into a patient's heart be minimally intrusive. For this reason, endocardial leads, which are introduced into a patient's vein, and subsequently anchored in the heart tissue, are preferred over epicardial leads, which typically require open chest surgery for implantation. Examples of epicardial leads are shown in U.S. Pat. Nos. 4,314,095, Device and Method for Making Electrical Contact, and 4,827,932, Implantable Defibrillation Electrodes.

Although less intrusive than epicardial leads, endocardial leads must pass through a vein and/or heart valve. It is therefore important to provide a lead with as small a diameter as possible, thereby minimizing or eliminating damage to fragile veins or impairment of valve function that may be caused by the lead. It is also critical to provide a highly flexible lead, both for ease of positioning and for long term behavior of the lead within a patient's beating heart. Increased flexibility extends the fatigue life of the lead in the heart and thus reduces the likelihood of a lead failure.

Examples of endocardial leads are shown in U.S. Pat. Nos. 4,679,572, Low Threshold Cardiac Pacing Electrodes, 4,662,382, Pacemaker Lead with Enhanced Sensitivity, 4,458,695, Multipolar Electrode Assembly for Pacing Lead, 4,161,952, Wound Wire Catheter Cardioverting Electrode, and 4,844,099/4,784,161, Porous Pacemaker Electrode Tip Using a Porous Substrate.

In a typical endocardial lead according to the prior art, the conductor and the electrode are coupled at a sleeve that must provide a low resistance electrical connection and a secure mechanical connection, while exhibiting a narrow profile to minimize intrusion of the lead in the patient's vein. Common practice is to join the conductor mechanically to the electrode at the sleeve portion by crimping. Such a joint is not optimal for endocardial applications as the sleeve must be both thick enough to provide sufficient strength to maintain a crimp bond, and have sufficient length to secure the crimp.

Electrical joints in implanted endocardial leads are subject to cyclical stresses, and should therefore be mechanically stable with respect to fatigue behavior. Because the lead is implanted into a human body, it must also be both biocompatible (i.e. non-toxic) and corrosion resistant. The best conductors, for example silver and copper, are both toxic and subject to corrosion within the human body.

Examples of various joints having application in medical electrical stimulation electrodes are shown in U.S. Pat. Nos. 4,161,952, found Wire Catheter Cardioverting Electrode, 4,214,804, Press Fit Electrical Connection Apparatus, and 4,328,812, Ring Electrode for Pacing Lead.

Bush et al, Electrical Connection for Medical Electrical Stimulation Electrodes, U.S. patent application Ser. No. 08/018,832, filed 18 Feb. 1993, discloses a cardiac lead that provides increased flexibility and smaller size than previous designs in the prior art. The lead described in Bush is formed by threading the distal end of a conductor through a sleeve, then bending the individual filars of the conductor back upon the surface of the sleeve. Crimping or resistance welding is used to join the electrode wires to the outer surface of the sleeve. When this method is used to join a conductor including a plurality of drawn silver filled tubes to the sleeve, a portion of the filling of each tube may need to be removed from the end of the tube. The tube is then flattened prior to being joined to the sleeve to minimize the possibility of leaching the toxic silver filling.

It would be highly desirable to provide a lead for medical electrical stimulation applications having low electrical resistance, high mechanical and fatigue strength, biocompatibility, and high corrosion resistance, while minimizing intrusiveness of the lead into the patient's body, minimizing lead thickness, and optimizing flexibility.

SUMMARY OF THE INVENTION

The present invention provides an improved lead construction for cardiac stimulation leads. In a preferred embodiment of the invention, the lead includes a sleeve which serves as an interface for joining a conductor to an electrode that comprises a plurality of electrode elements, which may be small coils. The sleeve defines a plurality of passages adapted for receiving the electrode elements, a passage for receiving the conductor, and, if desired, a passage for receiving one or more additional insulated conductors. The passages may be of any desired shape.

A conductor is joined to the sleeve by passing the distal end of the conductor through the passage in the sleeve and completely through the sleeve. The individual electrode elements are fitted into their respective passages in the sleeve such that an end of each electrode element passes through the sleeve. Additional insulated conductors may also be inserted through an optional passage formed in the sleeve for connection to additional lead electrodes.

In the preferred embodiment of the invention, the conductor is composed of a multifilar coil made of drawn filled tubing. A laser is used to weld filler material inserted within the conductor, and therefore the conductor, to a surface of the sleeve while preserving the shape of the conductor coil. Other methods such as resistance welding or brazing may be used to secure the conductor to the sleeve. The electrode elements are similarly secured inside respective passages of the sleeve.

In an alternate embodiment of the invention, the distal end of the conductor is fit over a hollow tube portion of the sleeve, and the distal ends of the electrode elements are inserted through their respective passages in the sleeve. Another embodiment provides a hollow tube portion extending from the distal face surface of the sleeve. The distal end of the conductor is inserted into a passage in the sleeve, and is extended into the hollow tube portion. Crimping is then used to secure the conductor to the sleeve. All of the passages defined by the sleeve may include chamfered edges, to minimize stress placed on the conductor at the joint.

A sleeve made in accordance with the present invention provides a narrow conductor/electrode joint that minimizes impact on the patient, while at the same time providing a cardiac lead that has excellent electrical properties, mechanical stability, and ease of manufacture, and that may be made from any desired material to thereby take advantage of new and/or improved materials. The present invention is readily practiced with any specified conductor material, such as MP35N/Ag drawn filled tubing, a low resistance conductor that exhibits excellent qualities of biocompatibility and corrosion resistance.

BRIEF DESCRIPTION OF THE DRAWINGS

FIG. 1 is a distal portion of a single pass defibrillation lead that includes a joint which is formed in accordance with the invention;

FIG. 2 is a distal portion of a right ventricular defibrillation lead that includes a joint which is formed in accordance with the invention;

FIG. 3 is a distal portion of a superior vena cava defibrillation lead that includes a joint which is formed in accordance with the invention

DETAILED DESCRIPTION OF THE INVENTION

The present invention provides an improved lead for cardiac stimulation in which the intrusiveness of the lead into the patient's body is minimized, while maintaining its high flexibility and performance.

A joint according to the invention is used in an endocardial defibrillation lead that connects an implantable cardioverter/defibrillator ("ICD") to a patient's heart. The lead includes an insulated conductor that transmits electrical pulses produced by the defibrillator to an electrode. The conductor and the electrode are joined at a sleeve. The specific configuration and location of electrodes is determined by the application for which the device is used. It should be appreciated that the invention is intended for use in other applications, in addition to the cardiac applications that are discussed herein for purposes of example.

FIGS. 1, 2, and 3 provide views that show, respectively, distal portions of a single pass defibrillation lead 40, a right ventricular (RV) defibrillation lead 50, and a superior vena cava (SVC) defibrillation lead 60, each of which includes at least one joint that is formed in accordance with the invention. Such joint is not noticeably wider than the electrode and additionally, the sleeve herein described does not have to be very long. Thus, the flexibility of the lead is not impaired by a long, rigid joint, as is the case in some prior art leads. In this way, the invention allows production of a lead that is minimally intrusive, both in length and in profile. Additionally, as freer, thinner conductor and electrode materials are introduced, the invention is readily adapted for use with such materials.

Figure 4A:
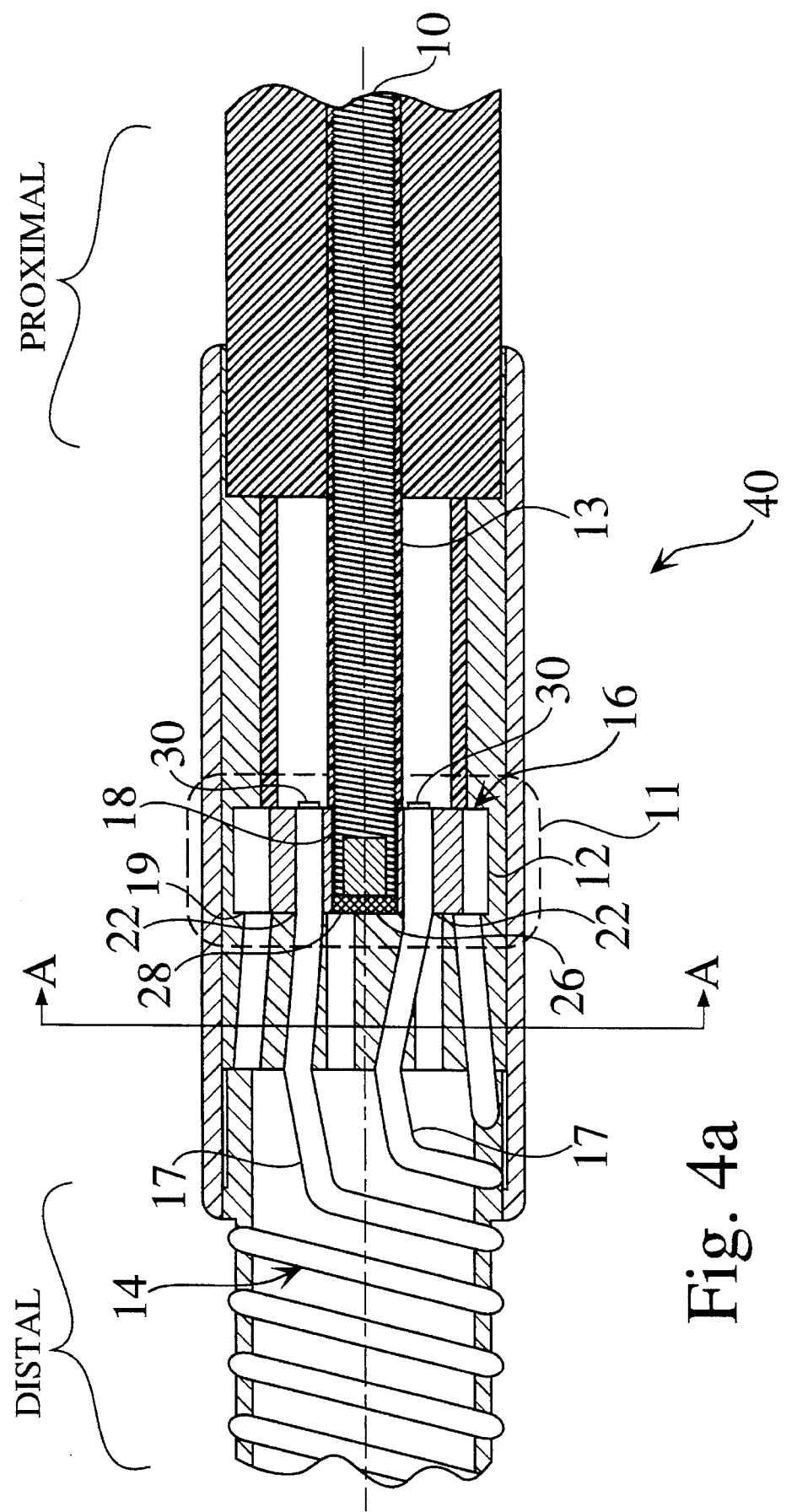
FIG. 4a is a longitudinal sectional view of the proximal joint of the single pass lead of FIG. 1 having a sleeve according to a first embodiment of the invention.

FIG. 4a provides a longitudinal sectional view of a single pass defibrillation lead 40 proximal joint having a sleeve 12 according to a first embodiment of the invention. In FIG. 4a, a joint is shown that includes a conductor 10, which may be, for example, of coil or cable construction. The conductor is joined to the sleeve 12 by inserting the distal end 26 of the conductor 10 into a passage 18 formed through the sleeve 12 (FIG. 4b) and passing the distal end of the conductor 10 completely through the sleeve 12. The portion of the conductor that protrudes beyond the distal face of the sleeve 12 has a filler material inserted into it. This is then laser welded to the sleeve with an ND:YAG laser to complete the connection.

An electrode 14 is also joined to the sleeve 12 by inserting the proximal ends of a plurality of electrode elements 17 through corresponding passages 22 formed through the sleeve (FIG. 4b), such that a proximal end of each electrode element 17 passes through to a proximal face surface 16 of the sleeve. The portions of the electrode elements 17 that protrude beyond the proximal face 16 of the sleeve are then laser welded to the sleeve 12 to complete the connection. A filler material may be used as discussed below. The joint is then overmolded with an overmolding material 11 to seal the assembly. For applications where the lead is used as a transvenous lead, the joint is preferably less than or equal to 0.121 inches O.D. after overmolding, and therefore, preferably less than or equal to 0.115 inches O.D. before overmolding.

Additional insulated conductors may be inserted through a passage 20 formed in the sleeve 12 to allow the passage of such conductors through the joint for connection to additional lead electrodes. Such conductors may be used, for example in leads having multiple electrodes for defibrillation, pacing, and/or sensing.

In the invention, the conductor 10 and electrode elements 17 may be formed of any selected material that provides a low resistance, biocompatible, corrosion resistant electrical path from a pulse generator, such as a pacemaker or a defibrillator, to an electrode. Thus, the invention allows the use of many different conductor materials, including solid conductors, wound conductors, tubular conductors, and stranded conductors.

In a preferred embodiment of the invention, the conductor may be made from a multifilar coil of drawn filled tubing, such as is supplied by Fort Wayne Metals of Fort Wayne, Ind. An insulator 13 typically surrounds the coil of conductor 10. Drawn filled tubing ("DFT") is composed of a very fine, flexible, hollow tube that is formed of a non toxic, corrosion resistant material, such as stainless steel or MP35N, which is an alloy made up of about 35% cobalt, 35% nickel, 20% chromium, and 10% molybdenum. The hollow inner portion of DFT is filled with a highly conductive material, such as silver(typically 22%–43% silver). Multiple strands of DFT are wound in parallel to form a multifilar coil. This structure therefore provides the tensile strength, corrosion resistance, fatigue resistance, and biocompatibility of MP35N or stainless steel with the high conductivity of silver.

In the preferred embodiment of the invention, a filler material 28,30 of MP35N may optionally be inserted into the open end of the conductor 10 and the electrode elements 17, respectively. A laser or other source of heat is then used to melt the filler material to form a weld bond between the conductor 10 or electrode 14 and sleeve 12 and seal the open end of the conductor 10 which generally prevents the silver filling from leaking therefrom, while maintaining the shape and structure of the DFT coil. The filler material 28, 30 also eliminates the support tubes or pins that would otherwise be necessary to maintain the integrity of the conductor 10 or electrode elements 17 for a crimp joint.

Laser welding is the preferred method for attaching the conductor 10 and electrode 14 to the sleeve. Laser welding produces a bond that does not require a sleeve having substantial wall thickness, as would be necessary if either the conductor or electrode were bonded to the sleeve mechanically, for example by a crimp.

Laser welding in accordance with the invention herein may be performed using any known technique and/or laser welding equipment that is appropriate for micro-welding. Other methods may be used to bond the conductor and electrode to the sleeve, for example resistance welding, brazing, or a conductive polymer may be used to form such bond.

The invention also allows the use of Pt/Ir 10% electrodes, which are highly conductive, biocompatible, and which exhibit excellent corrosion and fatigue resistance. Such electrodes are typically formed of multiple 0.003 inch filars wound to form a 0.012 inch O.D. coil, as described in Mar et al, U.S. patent application Ser. No. 08/126,629, which is commonly assigned to Ventritex, the assignee of the present application, and which is incorporated herein by this reference thereto. Because the invention allows the use of a sleeve in joining the conductor and the electrode to form the lead, the lead may be constructed of matched materials or dissimilar materials. Thus, the sleeve, electrodes, and conductor may each be formed of Pt/Ir 10% or MP35N, or may each be formed of different materials.

Figure 4B:
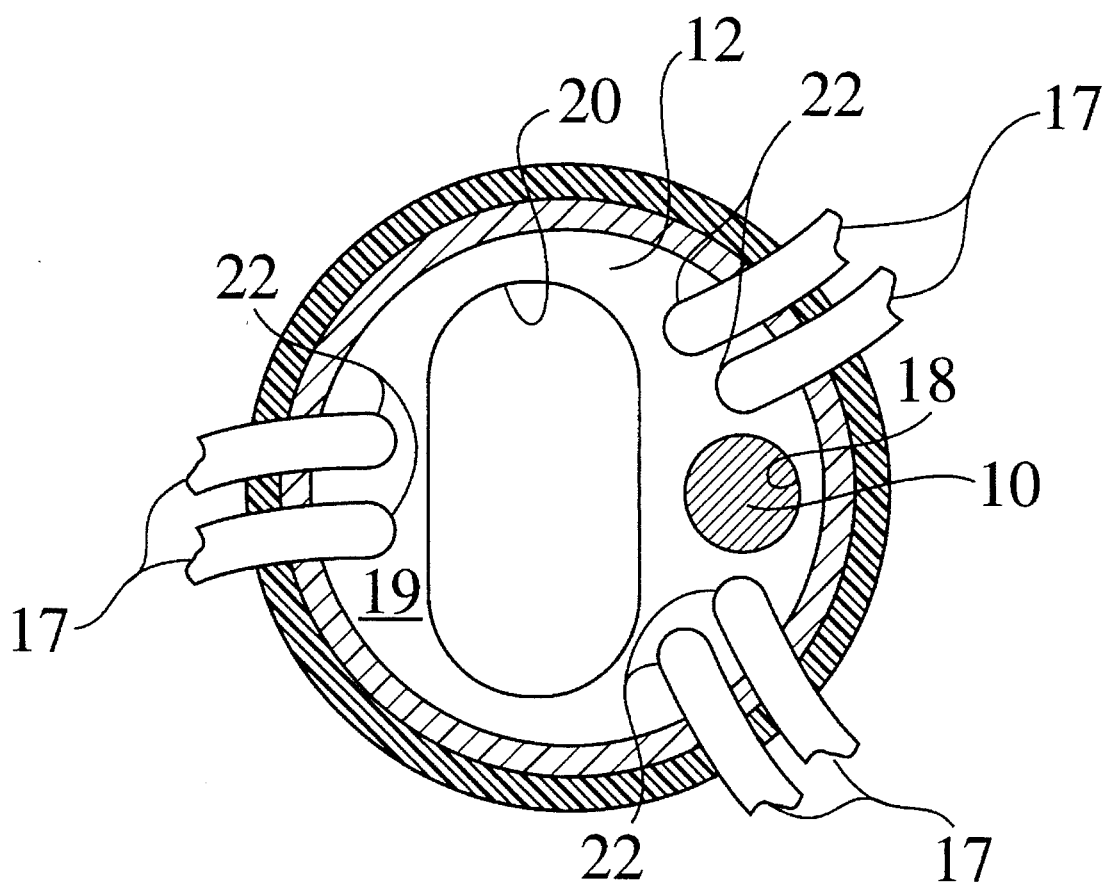
FIG. 4b is a sectional view at section line A—A in FIG. 4a showing the distal face surface of the single pass lead sleeve.

FIG. 4b is a transverse sectional view showing the distal face surface 19 of the single pass lead sleeve 12 shown at section line A—A in FIG. 4a. The distal face surface 19 of the sleeve 12 includes a passage 20 that is formed through the sleeve to receive one or more conductors. The number, size, shape and relative positioning of these passages may be varied according to the desired lead configuration. For example, the sleeve shown in FIGS. 4a and 4b is adapted to join a conductor 10 and an electrode 14 that is a formed of six electrode elements 17 which comprise small coils. All of the passages defined by the sleeve preferably include chamfered edges, to minimize stress placed on the conductor and electrode elements (see the related discussion below).

Figure 5:
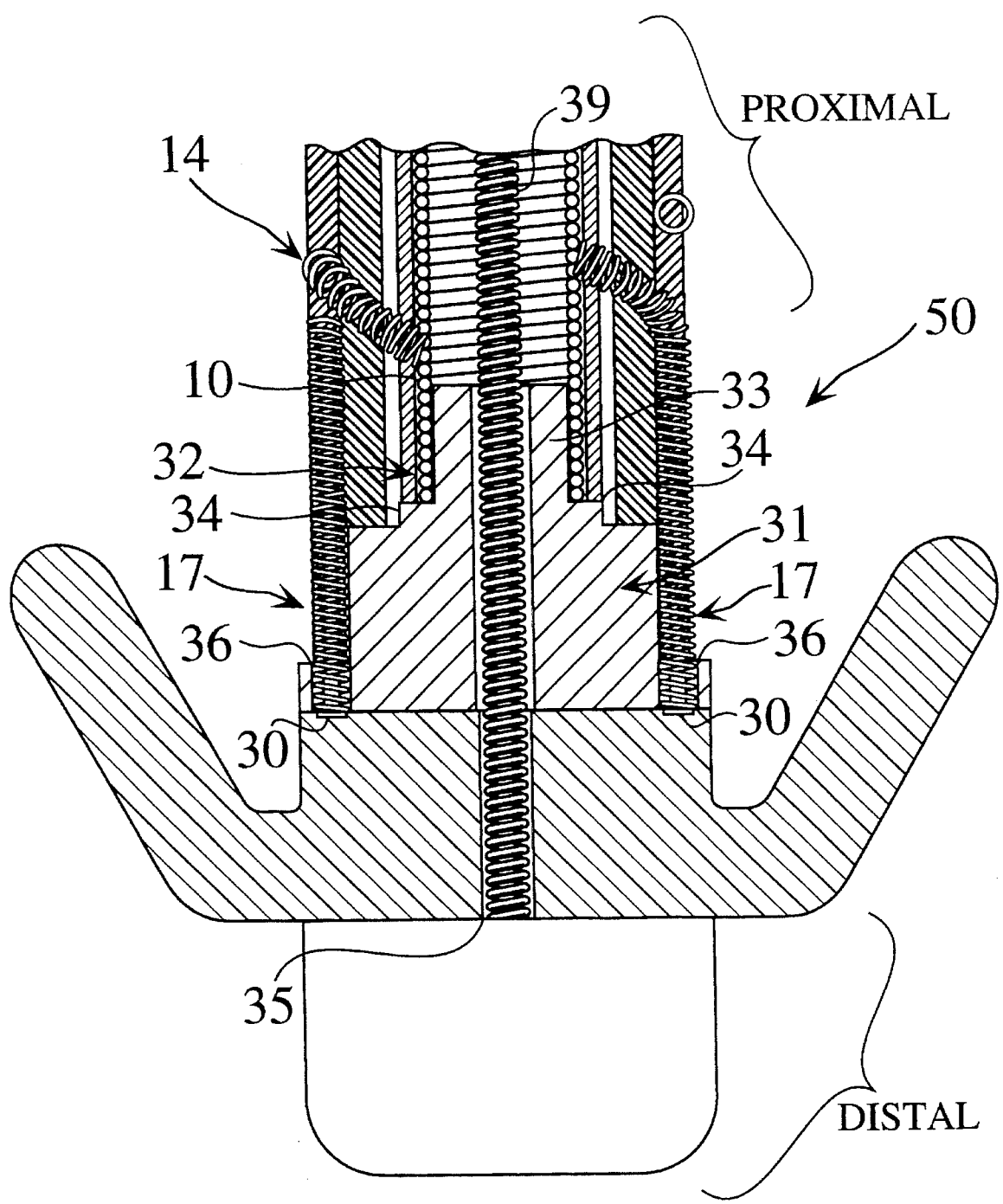
FIG. 5 is a longitudinal sectional view of a sleeve for use to form a distal joint in a distal electrode, for example for a right ventricular defibrillation lead according to an equally preferred embodiment of the invention.

FIG. 5 is a longitudinal sectional view of the distal portion of a lead 50, including a sleeve 31 for use to form a distal joint in a distal electrode, for example for a right ventricular defibrillation lead 50 according to an equally preferred embodiment of the invention. In the figure, the distal end 32 of the conductor 10 is fit over the hollow tube portion 33 of the sleeve 31; the electrode elements 17 are inserted through passages 36; and an optional filler 30 is inserted into the open ends of the coils that form the electrode elements. The filler is then melted with a laser, thus welding the electrode elements 17 to the sleeve 31.

The conductor is joined to the sleeve by melting step 34 with a laser, causing the material from step 34 to flow onto the coil. A passage 35 may be provided as a passageway for an additional insulated conductor 39 such as for connection to a distal pacing tip. If the electrode elements are strands, they may be welded without the use of a filler material.

Figure 6:
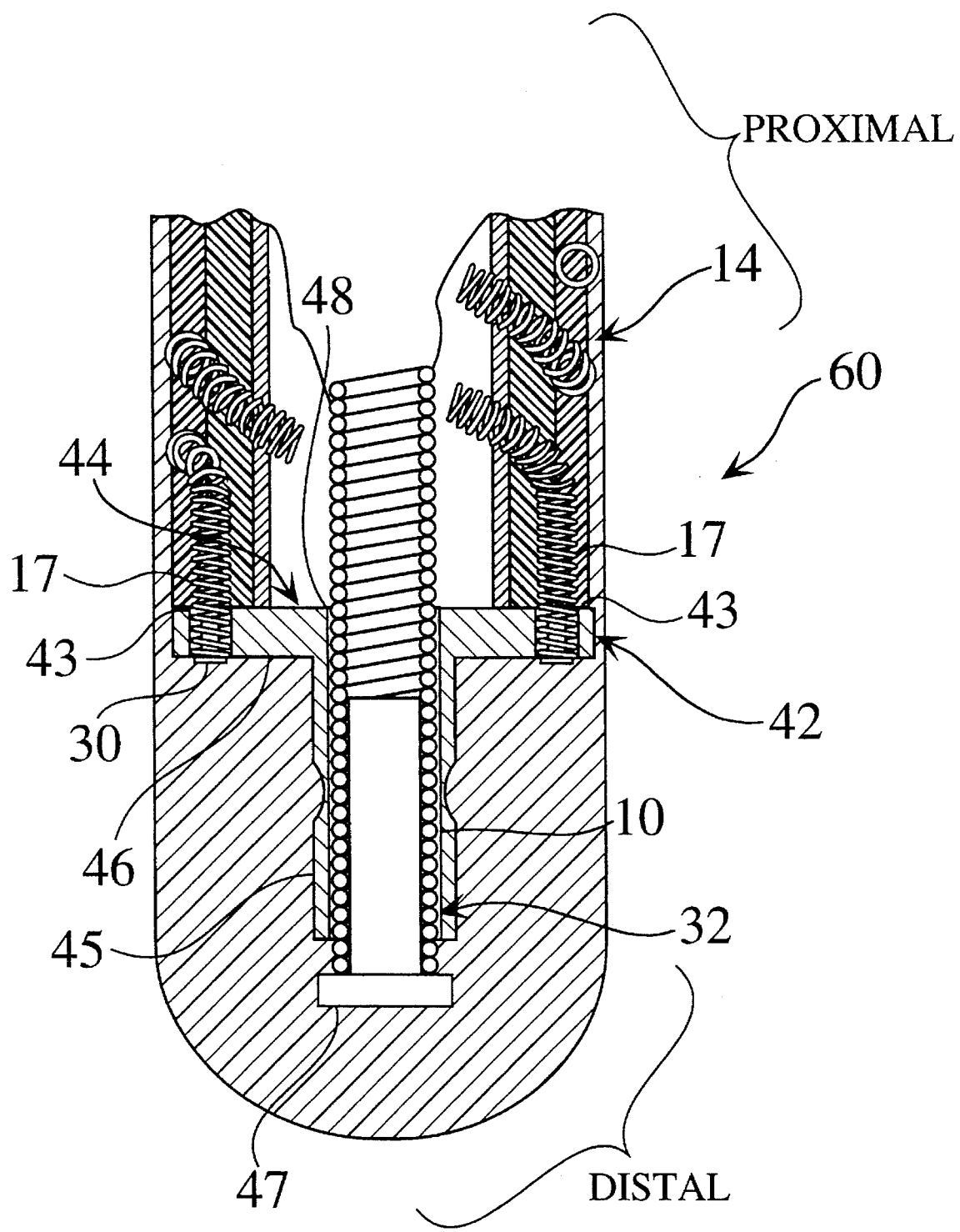
FIG. 6 is a sectional view of a sleeve that is useful for joining a conductor and electrode to form a superior vena cava defibrillation lead according to another equally preferred embodiment of the invention.

FIG. 6 is a sectional view of a sleeve 42 that is useful for joining a conductor and electrode to form an SVC defibrillation lead 60 according to another equally preferred embodiment of the invention. In the figure, a hollow tube portion 45 extends from the distal face surface 46 of the sleeve 42. The distal end 32 of the conductor 10 is inserted into a passage 48 in the proximal face surface 44 of the sleeve and extends into the hollow tube portion 45. A support pin 47 may be inserted in the distal end 32 of the conductor 10. Support pin 47 also functions as a stop for a positioning stylet to avoid the possibility of puncturing the end of the lead. The hollow tube portion 45 is then compressed to form a crimp that electrically and mechanically attaches the conductor to the sleeve. The electrode elements 17 are inserted into passages 43 formed through the sleeve, and an optional filler 30 is inserted into the open ends of the electrode elements. The electrode elements are then laser welded to the sleeve as discussed above.

Each passage formed in the sleeve may include a chamfer. The entry to the passage has a chamfered surface that provides a strain relief for the conductor or electrode. Absent the chamfer, the conductor or electrode element would confront a sharp edge at the point that it enters the passage that would stress the conductor or electrode and that could, in time, lead to failure of the electrical connection at the joint due to metal fatigue. The chamfer is typically 0.002 inches in depth and provides at a 45° angle relative to the inner surface of the passage.

Although the invention is described herein with reference to the preferred embodiment, one skilled in the art will readily appreciate that other applications may be substituted for those set forth herein without departing from the spirit and scope of the present invention. For example, the joint may be adapted for use in an epicardial lead. Accordingly, the invention should only be limited by the claims included below.

I claim:

1. A joint for a cardiac lead that includes a conductor and an electrode adapted for cardiac stimulation and including at least one electrode element, the joint comprising:

a sleeve having at least a first passage that is adapted to receive said conductor, and having at least a second passage that is adapted to receive said at least one electrode element, the sleeve having at least one face surface that provides a point of attachment for said at least one electrode element.

2. The joint of claim 1, wherein at least one of said first passage and said second passage extend through said sleeve.

3. The joint of claim 1, further comprising a hollow inner channel, said channel providing a pathway that is parallel to an axis of said first passage and adapted to pass an insulated conductor through and past said joint.

4. The joint of claim 1, said sleeve further comprising a hollow inner channel, said channel providing a pathway that is parallel to a conductor pathway and adapted to pass an additional insulated conductor through and past said sleeve.

5. The joint of claim 1, said sleeve flier comprising:

a hollow extension projecting from a sleeve surface and adapted to receive and mechanically retain a conductor therein, said extension being coaxial with said first passage.

6. A cardiac lead comprising:

an insulative lead body;

a connector on a proximal end of said lead body;

an electrode extending along a length of said lead body and comprising at least one electrode element;

a conductor passing through at least a portion of said lead body and electrically coupled to said connector at a proximal end;

a sleeve for electrically connecting said electrode element and said conductor and having opposing face surfaces and being positioned in said lead body, said sleeve having a first passage that is adapted to receive said conductor and a second passage that is adapted to receive said at least one electrode element; and wherein said conductor enters said first passage and said at least one electrode element enters said second passage through opposite surfaces of said sleeve.

7. A cardiac lead, comprising:

an insulative lead body;

a connector on a proximal end of said lead body;

an electrode extending along a length of said lead body and comprising at least one electrode element;

a conductor passing through at least a portion of said lead body and electrically coupled to said connector at a proximal end;

a tubular sleeve for electrically connecting said electrode element and said conductor and having opposing face surfaces and being positioned in said lead body, said sleeve having a first passage that is adapted to receive said conductor and a second passage that is adapted to receive a corresponding one of said at least one electrode element;

said at least one electrode element passing through said second passage and being bonded at one of said face surfaces; and said conductor being mechanically and electrically coupled to said sleeve at said second passage.

8. The lead of claim 7, wherein at least one of said conductor and said electrode element is a coil.

9. The lead of claim 7, wherein at least one of said conductor and said electrode element is a multifilar coil.

10. The lead of claim 7, wherein at least one of said electrode element and said conductor is laser welded to a respective sleeve face surface.

11. The lead of claim 8, further comprising:

a filler material placed near or within either or both of the electrode element and the conductor, said filler melting when exposed to a laser to effect a bond between said electrode element and/or conductor and said sleeve.

12. The cardiac lead of claim 7, said sleeve further comprising:

a hollow tubular extension projecting from one of said face surfaces in a coaxial fashion with said first passage and adapted to receive and mechanically retain said conductor.

13. The cardiac lead of claim 12 wherein a distal end of said conductor passes through said hollow tubular extension and said first passage.

14. The cardiac lead of claim 12 wherein a distal end of said conductor fits around said hollow tubular extension.

15. The cardiac lead of claim 7 wherein either or both of said conductor and said electrode element are bonded to said sleeve by laser welding using a filler material.

16. The cardiac lead of claim 7, said sleeve further comprising a hollow inner channel, said channel providing a pathway that is parallel to a conductor pathway and adapted to pass an additional insulated conductor through and past said sleeve.

17. The lead of claim 11, wherein said conductor is laser welded to an inner surface of said first passage.

18. The lead of claim 11, further comprising:

a filler material placed near or within either or both of the electrode and the conductor, said filler melting when exposed to a laser to effect a bond between said electrode and/or conductor and said sleeve.

19. A lead including a conductor and an electrode element and a sleeve for joining said conductor and said electrode element, the sleeve comprising:

a first passage adapted to receive said conductor therein where said conductor is joined to said sleeve by laser welding; and a second passage adapted to receive said electrode element therein, where said electrode element is joined to said sleeve by laser welding.

20. The lead of claim 19, wherein an end of the conductor is passed through the first passage and completely through the sleeve to a point of attachment; and wherein an end of the electrode element is passed through the second passage and completely through the sleeve to a point of attachment.

21. The sleeve of claim 19, further comprising:

a filler material placed near or within either or both of the electrode element and the conductor, said filler melting when exposed to a laser to effect a bond between said electrode element and/or conductor and said sleeve.

* * * * *